United States Patent
Chang

(10) Patent No.: US 6,524,277 B1
(45) Date of Patent: Feb. 25, 2003

(54) METHOD AND APPARATUS FOR AN INTRAVASCULAR DEVICE SHOWING FLASHBACK

(75) Inventor: Joseph J. Chang, Irving, TX (US)

(73) Assignee: Ethicon, Inc., Somerville, NJ (US)

( * ) Notice: Subject to any disclaimer, the term of this patent is extended or adjusted under 35 U.S.C. 154(b) by 46 days.

(21) Appl. No.: 09/752,491

(22) Filed: Dec. 29, 2000

(51) Int. Cl.[7] .............................................. A61M 5/162

(52) U.S. Cl. ........................... 604/164.02; 604/168.01; 604/170.01

(58) Field of Search ....................... 604/164.01, 164.02, 604/168.01, 170.01, 167.01

(56) References Cited

U.S. PATENT DOCUMENTS

| | | | | |
|---|---|---|---|---|
| 4,525,157 A | * | 6/1985 | Vaillancourt | 600/435 |
| 4,894,052 A | * | 1/1990 | Crawford | 604/507 |
| 5,295,970 A | * | 3/1994 | Clinton et al. | 604/168.01 |
| 5,704,914 A | * | 1/1998 | Stocking et al. | 604/164.07 |

* cited by examiner

*Primary Examiner*—Gene Mancene
*Assistant Examiner*—Arnold Castro
(74) *Attorney, Agent, or Firm*—Blakely, Sokoloff, Taylor & Zafman, LLP

(57) ABSTRACT

An apparatus related to an intravascular device that includes a housing coupled to a needle is claimed. A solid blunting member is coaxially nestled in the needle. An aperture or opening, located at a distal end of a side of the needle, is configured to allow fluid to flow into a space located between the needle and the catheter.

6 Claims, 4 Drawing Sheets

METHOD AND APPARATUS FOR AN INTRAVASCULAR DEVICE SHOWING FLASHBACK

BACKGROUND OF THE INVENTION

1. Field of the Invention

This invention relates generally to intravascular assemblies, and more specifically, to an intravascular assembly that provides an early indication of flashback.

2. Background

Intravascular devices such as catheter assemblies are generally used for passing fluids between a device such as a syringe or a drip to or from body lumens such as veins or arteries, or other internal target sites. Such an assembly usually includes a hub, and a catheter tube. The tube is typically secured to the hub by means of an eyelet ring that is press fit within the nose of the hub. This hub and tube assembly is then mounted over an introducer needle comprising a sharp needle attached to a plastic hub. The sharp tip of the needle, protruding from the catheter tip, is used for piercing a body lumen so that access may be gained into the body lumen by the needle and subsequently the catheter. The needle may have a hollow blunting member within the needle. A blunting member is a safety element that is typically activated once the health care worker has taken blood from a patient. Upon activation, the hollow blunting member extends past the distal tip of the needle and prevents the needle from puncturing a person.

Some intravascular devices that include hollow blunting members show flashback. Flashback is, for example, blood from a patient that is visibly entering an intravascular device. However, conventional intravascular devices use extremely limited space for early flashback. An extended period of time is needed when using conventional intravascular devices in order to view the blood flowing into the needle. This defeats the purpose of using such a conventional intravascular device. It is therefore desirable to have an apparatus that addresses this disadvantage.

SUMMARY

The invention involves an intravascular device that shows flashback after the intravascular device has been inserted into a patient. One embodiment of the invention relates to an intravascular device that includes a housing coupled to a needle. A solid blunting member is coaxially nestled in the needle. An aperture, located at a distal end of the needle, is configured to allow fluid to flow into a space located in the needle. Additional features, embodiments, and benefits will be evident in view of the figures and detailed description presented herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention in which.

DETAILED DESCRIPTION

The invention involves an intravascular device that provides an early indication of flashback of a fluid such as blood from a patient. Flashback indicates that a vein has been entered and the intravascular device does not need to be inserted further into the patient's vein. One embodiment of the invention includes a housing coupled to a needle in which a solid blunting member is coaxially nestled in the needle. An aperture or opening, located at a distal end of the side of the needle, is configured to allow fluid to flow into an annular space located in the needle thereby providing early flashback.

Referring to the figures, exemplary embodiments of the invention will now be described. The exemplary embodiments are provided to illustrate aspects of the invention and should not be construed as limiting the scope of the invention.

Figure 1:
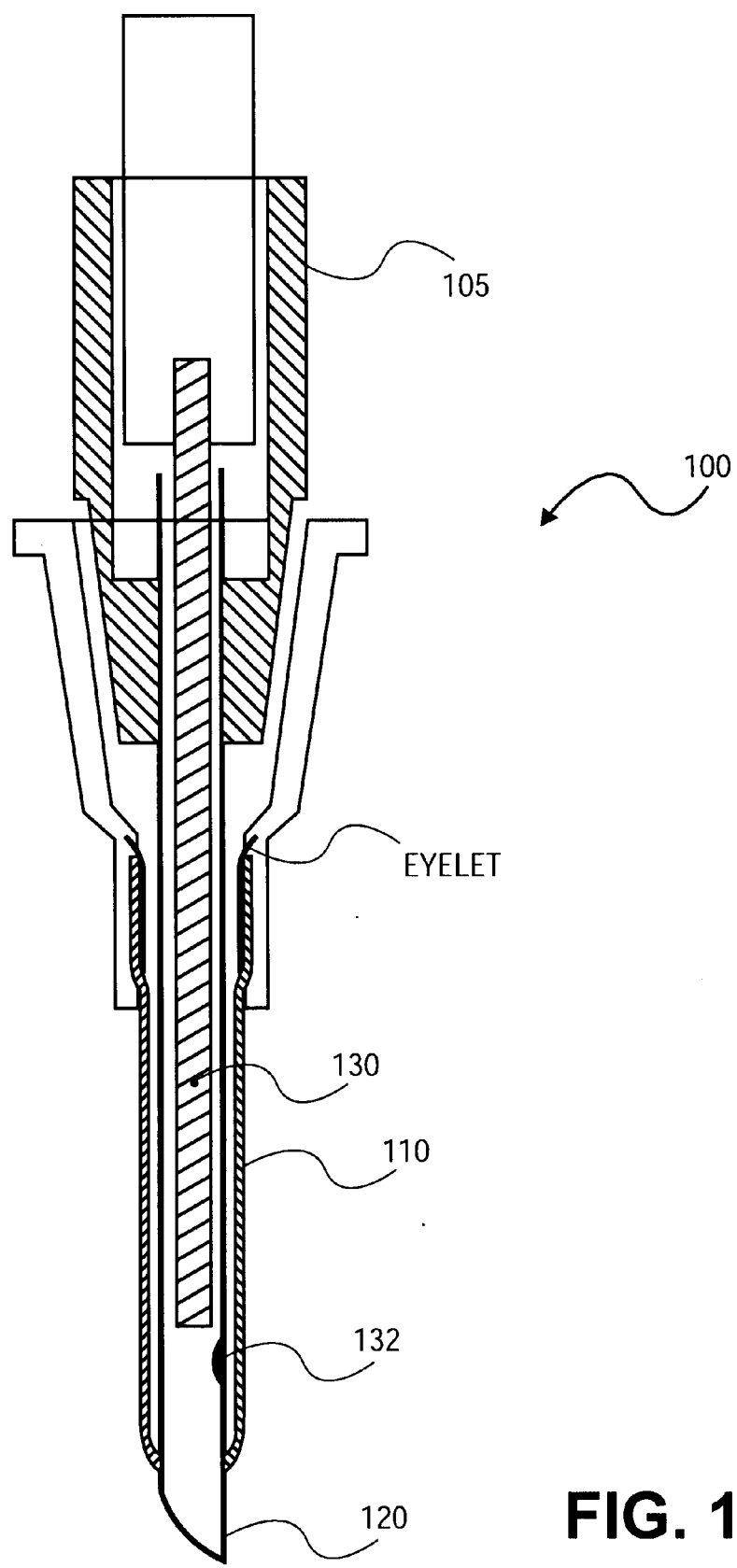
FIG. 1 illustrates a schematic cross-sectional view of an intravascular assembly in accordance with one embodiment of the invention.
Figure 2:
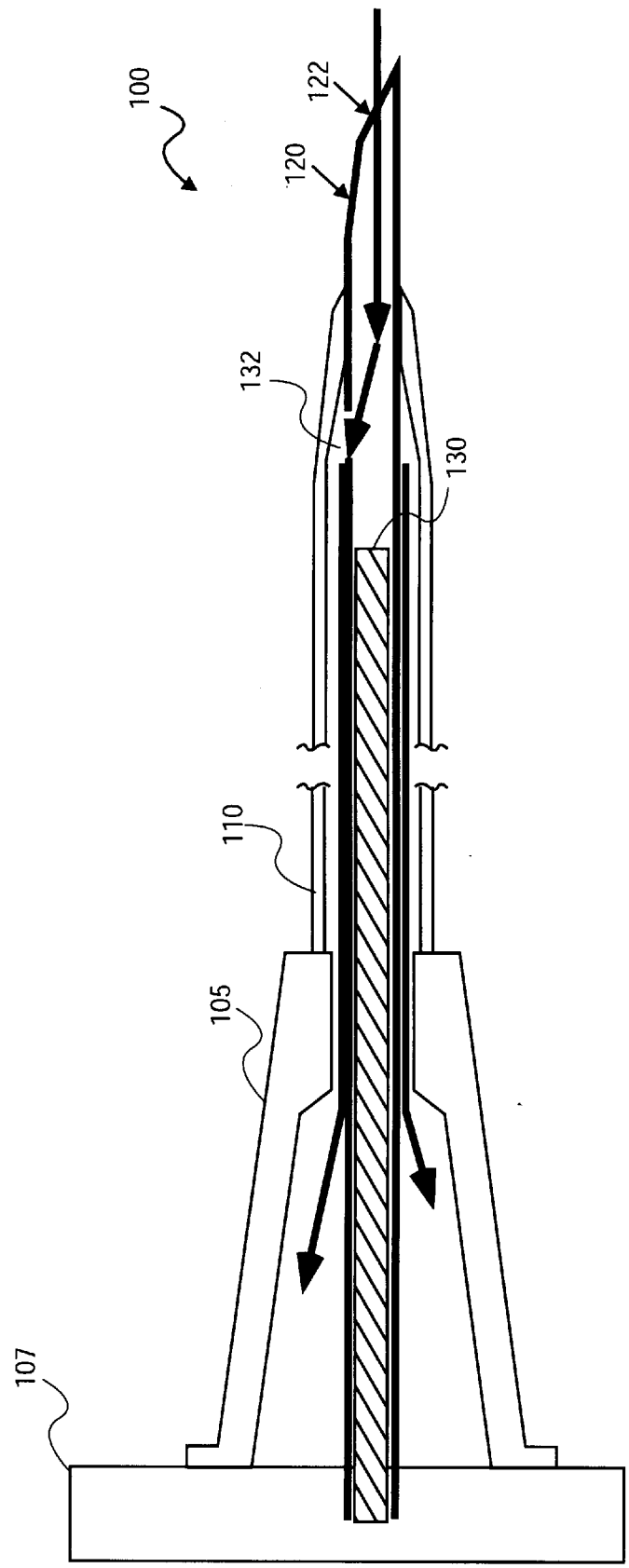
FIG. 2 illustrates a schematic cross-sectional view of the intravascular assembly of FIG. 1 in which a fluid flows through the intravascular assembly in accordance with one embodiment of the invention.

FIGS. 1 and 2 illustrate schematic cross-sectional view of intravascular assembly 100 in accordance with one embodiment of the invention. Intravascular assembly 100 includes hub 105 coupled to tube 110 using conventional means. Hub 105 and tube 110 may also be formed as a one-piece or two-piece assembly. Needle 120 is coupled to hub 105 and extends into tube 110.

The proximal or non-puncturing end of needle 120 is coupled to hub 105 and tube 110 using conventional means. It will be appreciated that hub 105 and needle 120 are configured to prevent blood from flowing out of intravascular assembly 100 but air is still allowed to vent from intravascular assembly 100 through needle holder 107 connected to a vent plug (not shown). Needle 120, having a length of about 0.5 inches to about 4 inches, extends through hub 105 and is further coupled to a needle holder 107.

Solid blunting member 130, having a length that ranges from about 0.5 inches to about 4 inches, is inserted inside needle 120. The distal end of blunting member 130 is placed about 0.050 inches to about 0.300 inches in distance from distal tip of needle 120. This may be accomplished in a variety of ways. For example, the distal portion of solid blunting member 130 is aligned with the proximal portion of needle 120. Solid blunting member 130 is then inserted into needle 120. Solid blunting member 130 slides securely into needle 120.

FIG. 2 illustrates the flow of blood through intravascular assembly 100 of FIG. 1. Blood enters distal tip 122 of needle 120 until the blood then contacts distal end of blunting member 130. Solid blunting member 130 then prevents, either completely or substantially, fluid from flowing through the remainder of a substantial portion of the inner diameter of hollow needle 120. This is accomplished by having the diameter of solid blunting member 130 range from about 0.010 to about 0.080 inches and the inner diameter of needle 120 range from about 0.012 inches to about 0.082 inches, so that there is little if any room for fluid to pass between needle and blunting member. The blood then travels away from blunting member 130. The blood enters aperture(s) 132 located on a side of needle 120. Aperture 132 provides an early indication of the blood flashback. The blood continues to travel through an annular space defined by needle 120 and tube 110. The blood then flows into hub 105 and through needle holder 107 and collects in a flashback chamber.

Figure 3:
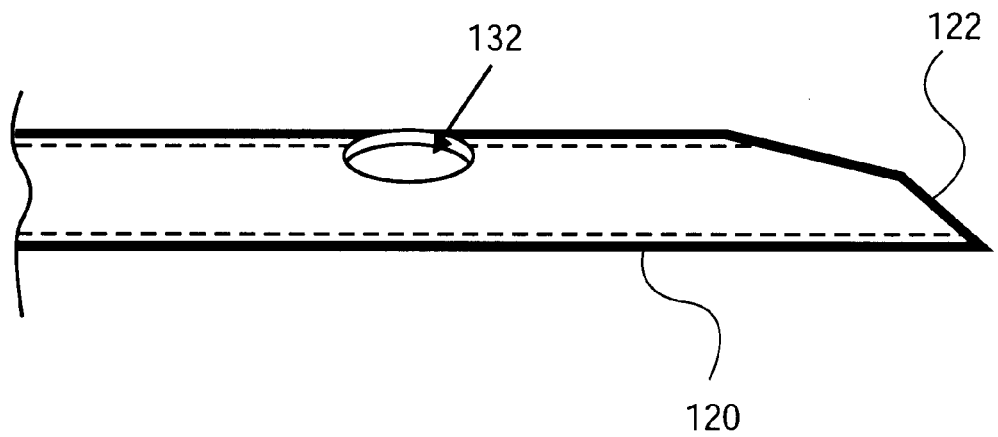
FIG. 3 illustrates a schematic cross-sectional view of a needle with an aperture located in a side of a needle in accordance with one embodiment of the invention.

FIGS. 1 through 3 illustrate needle 120 with aperture 132 located in a side of needle 120. The diameter of aperture 132 that allows blood to enter annular space may range from about 0.005 inches to about 0.075 inches. The length of annular space may range from about 0.4 inches to about 3.5 inches. It will be appreciated that the dimensions of aperture 132 may depend upon the gauge of the needle.

Figure 4:
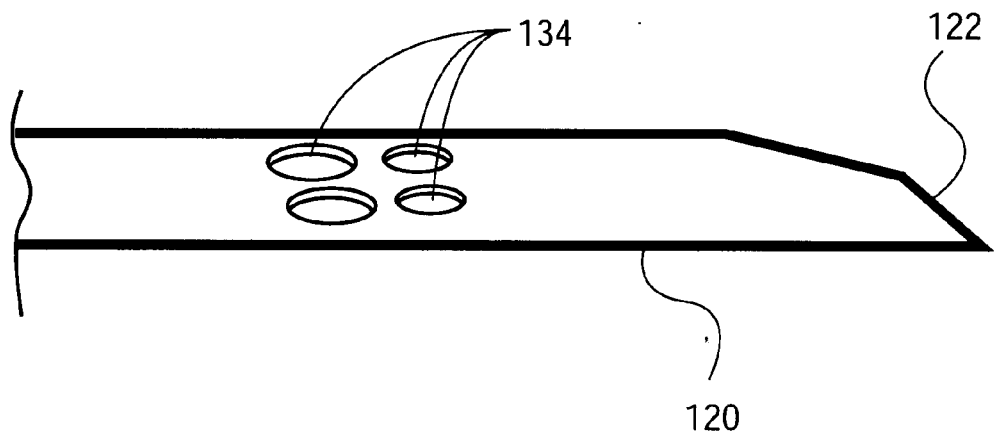
FIG. 4 illustrates a schematic cross-sectional view of a needle with a plurality of apertures located in the side of a needle in accordance with one embodiment of the invention.

In another embodiment, needle 120 may have a plurality of apertures to provide visual flashback. The plurality of apertures 134 are located at the distal end of needle 120 as illustrated in FIG. 4. Generally, the number of apertures may be determined by the diameter of each aperture and by the size of the needle. Plurality of apertures 134 have a diameter of about 0.005 inches to about 0.050 inches. Typically, there are less than five apertures located at the distal end of needle 120. After the blood enters plurality of apertures 134, the blood enters an annular space of needle 120 that extends from about 0.4 inches to about 3.5 inches. Additionally, the annular space of needle 120 has a diameter from about 0.005 inches to about 0.075 inches.

Figure 5:
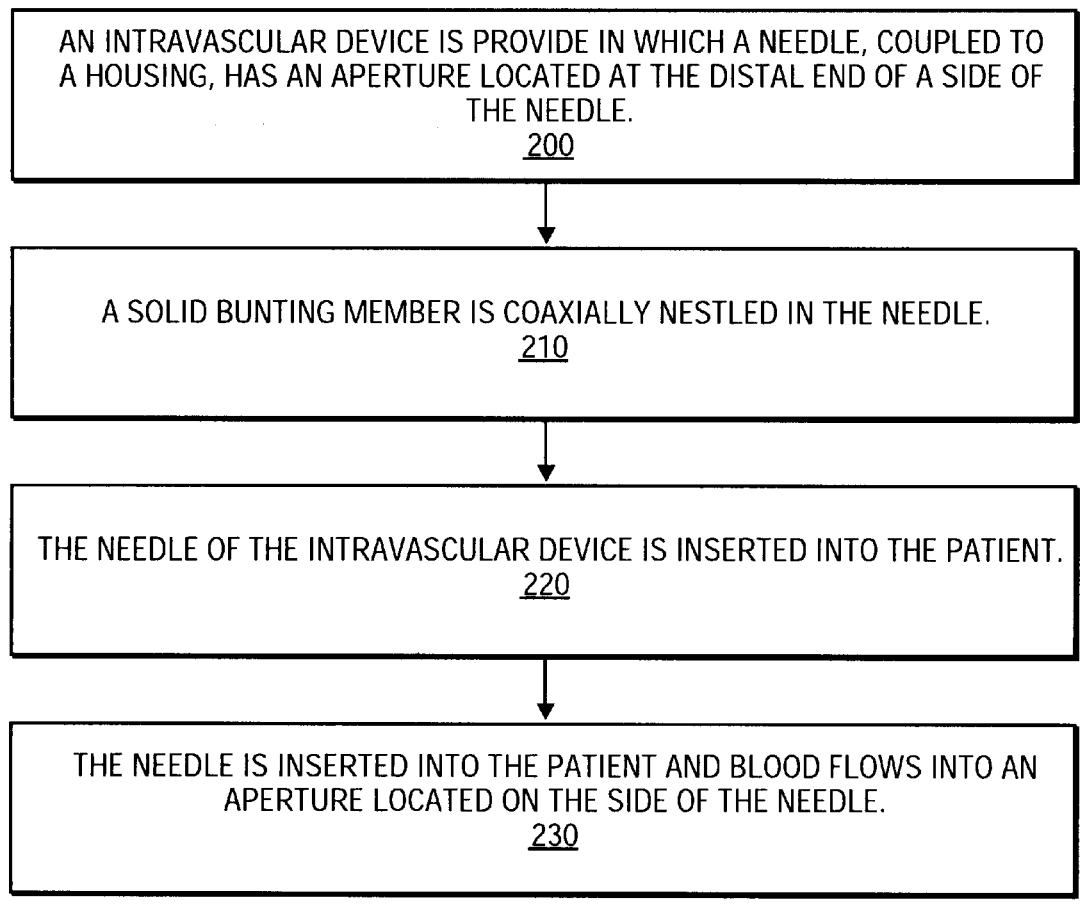
FIG. 5 illustrates a flow diagram of one method in accordance with one embodiment of the invention.

FIG. 5 illustrates a block diagram for forming and using an intravascular device in accordance with one embodiment of the invention. At block 200, a needle is coupled to a housing. The needle has an aperture located at a distal end of a side of the needle. At block 210, a solid blunting member is coaxially nestled in the needle. At block 220, the needle of the intravascular device is inserted into a patient. At block 230, a fluid such as blood flows into the needle and is prevented by solid blunting member from passing directly through the needle. Instead, the blood enters an aperture located on a side of the needle and passes through an annular space in the needle. Once the health care worker has completed his or her task, the needle is withdrawn and the blunting member is engaged causing the blunting member to slidably move past the distal tip of the needle. This prevents the needle from inadvertently harming another person.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An intravascular device comprising:

a housing;

a needle coupled at a proximal end to the housing, the needle having at least one opening in a cylindrical portion of the needle located adjacent a distal end of the needle;

a solid blunting member coaxially nestled in the needle wherein the at least one opening in the needle is configured to allow fluid to flow into a hollow bore of the needle until the fluid contacts the solid blunting member and enters an annular space located between the needle and a catheter.

2. The intravascular device of claim 1, wherein the solid blunting member is configured to slide inside the needle.

3. A catheter unit comprising:

a housing;

the housing coupled to a tube and to a proximal end of a needle having at least one hole in a cylindrical portion of the needle adjacent a distal end of the needle to allow fluid to flow into an annular space between the needle and the housing; and a solid blunting member coaxially nestled in the needle.

4. The catheter unit of claim 3, wherein the solid blunting member is configured to slide inside the needle.

5. A method comprising:

providing an intravascular device having a proximal end of a needle coupled to a housing, the needle has an aperture to provide flashback located adjacent a distal end of the needle;

inserting a solid blunting member into the needle;

inserting the needle of the intravascular device into a patient; and allowing blood to flow into the aperture and away from the solid blunting member into an annular space between the needle and the housing.

6. The method of claim 5, wherein the solid blunting member is configured to slide inside the needle.

* * * * *